United States Patent
Rose et al.

[11] Patent Number: 5,685,881
[45] Date of Patent: Nov. 11, 1997

[54] AROMATIC ALLYLAMINONITRO COMPOUNDS, HAIR DYE COMPOSITIONS CONTAINING AROMATIC ALLYLAMINONITIO COMPOUNDS, AND SYNTHETIC AND NATURAL FIBER DYEING PROCESS

[75] Inventors: David Rose, Hilden; Horst Hoeffkes; Edgar Lieske, both of Duesseldorf; Iduna Matzik, Ekrath, all of Germany

[73] Assignee: Henkel Kommanditgesellschaft auf Aktien, Duesseldorf, Germany

[21] Appl. No.: 448,448

[22] PCT Filed: Nov. 25, 1993

[86] PCT No.: PCT/EP93/03303

§ 371 Date: Jun. 30, 1995

§ 102(e) Date: Jun. 30, 1995

[87] PCT Pub. No.: WO94/12149

PCT Pub. Date: Jun. 9, 1994

[30] Foreign Application Priority Data

Dec. 3, 1992 [DE] Germany .................. 42 40 684.6

[51] Int. Cl.⁶ .................. A61K 7/13; C07C 211/52
[52] U.S. Cl. .................. 8/405; 8/404; 8/605; 564/441; 564/443
[58] Field of Search .................. 564/305, 441, 564/443; 8/404, 405, 414, 415, 649, 636, 605

[56] References Cited

U.S. PATENT DOCUMENTS

| | | | |
|---|---|---|---|
| 3,117,911 | 1/1964 | Kalopissis et al. | 167/88 |
| 3,274,249 | 9/1966 | Brunner et al. | 260/573 |
| 3,442,639 | 5/1969 | Soper | 564/441 |
| 3,518,309 | 6/1970 | Soper | 564/441 |
| 3,861,868 | 1/1975 | Milbrada | 8/414 |
| 4,077,795 | 3/1978 | Cooke et al. | 564/441 |
| 4,619,666 | 10/1986 | Rose et al. | 8/414 |
| 4,877,880 | 10/1989 | Woolard | 548/190 |
| 5,189,220 | 2/1993 | Desmurs et al. | 564/404 |
| 5,254,655 | 10/1993 | Gibbons et al. | 528/15 |

FOREIGN PATENT DOCUMENTS

| | | |
|---|---|---|
| 699018 | 12/1964 | Canada . |
| 0353130 | 1/1990 | European Pat. Off. . |
| 0378463 | 7/1990 | European Pat. Off. . |
| 1170583 | 7/1959 | Germany . |
| 1299002 | 10/1961 | Germany . |
| 1569808 | 7/1970 | Germany . |
| 1924249 | 6/1978 | Germany . |
| 3425151 | 1/1986 | Germany . |

*Primary Examiner*—Paul Lieberman
*Assistant Examiner*—Caroline L. Dusheck
*Attorney, Agent, or Firm*—Ernest G. Szoke; Wayne C. Jaeschke; Real J. Grandmaison

[57] ABSTRACT

Aromatic allylaminonitro compounds corresponding to formula (I):

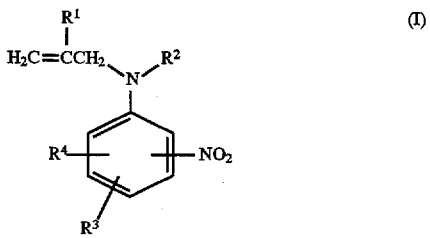

in which $R^1$ is hydrogen or an alkyl group containing 1 to 4 carbon atoms, $R^2$ is hydrogen, an alkyl group containing 1 to 4 carbon atoms or an allyl group $CH_2C(R^5)=CH_2$, where $R^5$ is hydrogen or an alkyl group containing 1 to 4 carbon atoms, $R^3$ is carboxyl, hydroxy, nitro, halogen or a group $NR^6R^7$, where $R^6$ and $R^7$ independently of one another represent hydrogen, an alkyl group containing 1 to 4 carbon atoms, a hydroxyalkyl or dihydroxyalkyl group containing 2 to 4 carbon atoms or an allyl group $CH_2C(R^8)=CH_2$, where $R^8$ is hydrogen or an alkyl group containing 1 to 4 carbon atoms, and $R^4$ is hydrogen or nitro, with the proviso that $R^3$ and $R^4$ are not both nitro. The compounds are useful for dyeing fibers, particularly human hair.

11 Claims, No Drawings

AROMATIC ALLYLAMINONITRO COMPOUNDS, HAIR DYE COMPOSITIONS CONTAINING AROMATIC ALLYLAMINONITIO COMPOUNDS, AND SYNTHETIC AND NATURAL FIBER DYEING PROCESS

BACKGROUND OF THE INVENTION

1. Field of the Invention

This invention relates to new dyes of aromatic allylaminonitro compounds for dyeing fibers of natural origin and synthetic fibers.

Substantive dyes play a prominent part in dyeing technology. In the context of the present invention, a substantive dye is a dye which is directly absorbed onto the fibers from a medium suitable for the particular dye finish to be obtained.

2. Discussion of Related Art

Aromatic nitro compounds substituted by at least one other alkylamino or hydroxyalkylamino group are an important group of substantive dyes. Corresponding aromatic nitro compounds are described, for example in DE-PS 12 99 002, in DE-OSS 34 25 151 and 15 69 808 and in DE-AS 11 70 583.

However, only a few aromatic nitro compounds containing an additional allylamino group are known. The present invention relates to new aromatic allylaminonitro compounds which are eminently suitable for the dyeing of fibers of natural origin and synthetic fibers.

DESCRIPTION OF THE INVENTION

The present invention relates to aromatic allylaminonitro compounds corresponding to formula (I):

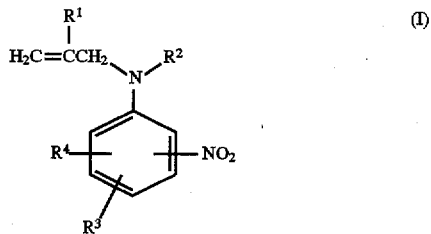

in which $R^1$ is hydrogen or an alkyl group containing 1 to 4 carbon atoms, $R^2$ is hydrogen, an alkyl group containing 1 to 4 carbon atoms or an allyl group $CH_2C(R^5)=CH_2$, where $R^5$ is hydrogen or an alkyl group containing 1 to 4 carbon atoms, $R^3$ is carboxyl, hydroxy, nitro, halogen or a group $NR^6R^7$, where $R^6$ and $R^7$ independently of one another represent hydrogen, an alkyl group containing 1 to 4 carbon atoms, a hydroxyalkyl or dihydroxyalkyl group containing 2 to 4 carbon atoms or an allyl group $CH_2C(R^8)=CH_2$, where $R^8$ is hydrogen or an alkyl group containing 1 to 4 carbon atoms, and $R^4$ is hydrogen or nitro, with the proviso that $R^3$ and $R^4$ are not both nitro.

In a preferred embodiment, the invention relates to aromatic allylaminonitro compounds corresponding to formula I, in which the $NO_2$ group is in the para position to the allylamino group $N(R^2)CH_2C(R^1)=CH_2$, $R^3$ is hydroxy and $R^4$ is hydrogen.

In another preferred embodiment, the invention relates to aromatic allylaminonitro compounds corresponding to formula I, in which the $NO_2$ group is in the ortho position to the allylamino group $N(R^2)CH_2C(R^1)=CH_2$, $R^3$ represents $NR^6R^7$ and is in the para position to the allylamino group $N(R^2)CH_2C(R^1)=CH_2$ and $R^4$ is hydrogen. Particularly preferred aromatic allylamino compounds corresponding to formula I are those in which $R^1$ and $R^2$ are hydrogen and $R^6$ and $R^7$ are identical groups. 3-Nitro-4-allylamino-aminobenzene is most particularly preferred.

The present invention also relates to the use of aromatic allylaminonitro compounds corresponding to formula I for the dyeing of fibers of natural origin and synthetic fibers.

Fibers of natural origin are understood to be human, animal and vegetable fibers, for example silk, cotton, linen, jute and sisal, and keratin fibers, such as hairs, pelts, wool or feathers, and also regenerated or modified natural fibers, for example viscose, nitrocellulose and acetyl cellulose, alkyl, hydroxyalkyl and carboxyalkyl celluloses. Examples of synthetic fibers are polyamide, polyester, polyacrylonitrile and polyurethane fibers.

The compounds corresponding to formula I may be used both as such and in the form of their water-soluble salts. Water-soluble salts are understood to be such salts as, for example, the hydrochlorides or hydrobromides. It is not necessary to use an individual compound of formula I, instead a mixture of various compounds corresponding to formula I may also be used. The dyes corresponding to formula I produce colors over a broad range from orange-brown to blue-violet, their capacity for absorption onto the fibers and their level-dyeing behavior being above-average. In addition, the dye finishes obtained are distinguished by very good fastness to light, perspiration and washing.

The dyeing of textile fibers is preferably carried out by the absorption method at temperatures above 90° C., although other dyeing processes typically used for the dyeing of textile fibers are also suitable.

However, the aromatic allylaminonitro compounds corresponding to formula I are preferably used for dyeing keratin fibers, more particularly human hair, because they are absorbed onto, and intensively color, keratin fibers or rather human hair at physiologically tolerable temperatures below 40° C. It is pointed out in this regard that the dyes used in the dyeing of hair and the colors obtained have to meet particular requirements. The dyes have to be dermatologically and toxicologically safe, must be absorbed onto the hair at low temperatures and, at the same time, are required to show good level-dyeing behavior. The colors obtained have to be resistant to hair treatment methods including, for example, permanent waving. These stringent requirements are satisfied particularly effectively by the aromatic allylaminonitro compounds corresponding to formula I and the colors obtained with them.

The present invention also relates to hair dye formulations containing dyes of formula I as claimed in claims 1 to 3 in a quantity of 0.01 to 5% by weight and preferably in a quantity of 0.1 to 2% by weight, based on the hair dye formulation as a whole, and a water-containing cosmetic carrier.

Water-containing cosmetic carriers are, for example, creams, emulsions, gels or even surfactant-containing foaming solutions, for example in shampoos, foam aerosols or other preparations suitable for application to the hair.

Typical constituents of such water-containing cosmetic preparations are, for example, wetting agents and emulsifiers, such as anionic, nonionic and ampholytic surfactants, for example fatty alcohol sulfates, alkanesulfonates, α-olefin sulfonates, fatty alcohol polyglycol ether sulfates, ethylene oxide adducts with fatty alcohols, fatty acid and alkylphenols, sorbitan fatty acid esters and fatty acid partial glycerides, fatty acid alkanolamides, and thickeners such as, for example, methyl or hydroxycellulose, starch, fatty alcohols, paraffin oils, fatty acids, also perfume oils and hair-care additives such as, for example, water-soluble cationic, ampholytic and anionic polymers, protein derivatives, pantothenic acid and cholesterol. The constituents of the cosmetic carriers are used in typical quantities for the production of the hair dye formulations according to the invention. For example, emulsifiers are used in concentrations of 0.5 to 30% by weight while thickeners are used in concentrations of 0.1 to 25% by weight, based on the hair dye formulation as a whole.

Other typical substantive dyes, for example other nitrobenzene derivatives, anthraquinone dyes, triphenyl methane or azo dyes, or even typical oxidation hair dye precursors, where a distinction has to be drawn between primary and secondary intermediates, may be added to the aromatic allylaminonitro compounds corresponding to formula I to modify the colors obtained. Primary intermediates form the oxidation hair dyes by oxidative coupling with one another or optionally in the presence of suitable secondary intermediates. The primary intermediates used include, for example, primary aromatic amines containing another free or substituted hydroxy or amino group in the para position or ortho position, diamino-pyridine derivatives, heterocyclic hydrazones, 4-amino-pyrazolone derivatives and 2,4,5,6-tetraaminopyrimidine and derivatives thereof. The secondary intermediates include metaphenylene diamine derivatives, naphthols, resorcinol and resorcinol derivatives, pyrazolones and meta-aminophenols.

Other substantive dyes and oxidation hair dye precursors may be present in a quantity of 0.01 to 5% by weight and preferably in a quantity of 1 to 3% by weight, based on the hair dye formulation as a whole.

The hair dye formulations according to the invention may be used irrespective of the nature of the cosmetic preparation, for example as a cream, gel or shampoo, in a mildly acidic, neutral or alkaline medium. The hair dye formulations are preferably used at pH values in the range from 6 to 10. The temperatures at which they are used are in the range from 15° C. to 40° C. After a contact time of around 30 minutes, the hair dye formulation is removed from the hair to be dyed by rinsing. The hair is then washed with a mild shampoo and dried. There is no need for washing with a shampoo in cases where a carrier of high surfactant content, for example a dye shampoo, has been used.

The following Examples are intended to illustrate the invention without limiting it in any way.

EXAMPLES

Production Examples 1. 3-Nitro-4-allylamino-aminobenzene

A mixture consisting of 4-fluoro-3-nitroaminobenzene (7.8 g, 0.05 mole) and allylamine (7.1 g, 0.125 mole) was heated under reflux for 8 hours. After cooling, the product was filtered off under suction and recrystallized from ethanol/water. Dark red crystals, melting point 80°–83° C.

2. 3-Nitro-4-allylamino-N,N-bis-(2-hydroxyethyl)-amino-benzene

Synthesis and working up same as for compound 1, but with 4-fluoro-3-nitro-N,N-bis-(2-hydroxyethyl)-aminobenzene instead of 4-fluoro-3-nitroaminobenzene. Black crystals, melting point 73°–75° C.

3. 3-Nitro-4-allylamino-N,N-bis-(2,3-dihydroxypropyl)-aminobenzene

Synthesis as for compound 1, but with 4-fluoro-3-nitro-N,N-bis-(2,3-dihydroxypropyl)-aminobenzene instead of 4-fluoro-3-nitroaminobenzene. Working up: the reaction mixture was concentrated and the dark oil was dissolved in ethanol. Compound (3) was then precipitated with HCl gas in the form of the hydrochloride. Yellow crystals, melting point 154°–158° C.

4. 3-Nitro-4-diallylamino-N-(2-hydroxyethyl)-aminobenzene

A mixture consisting of 1-(2-hydroxyethyl)-amino-2-nitro-4-aminobenzene (9.8 g, 0.05 mole), allyl bromide (6.1 g, 0.05 mole) and potassium carbonate (3.5 g, 0.025 mole) in 80 ml of ethanol was boiled under reflux for 6 hours. After cooling, the reaction mixture was filtered under suction and the residue was extracted with ether. By introducing HCl gas, the product was precipitated in the form of the hydrochloride and subsequently filtered under suction. Yellow crystals, melting point 166°–170° C.

5. 3-Nitro-4-allylamino-N,N-bis-(allyl)-aminobenzene

A mixture consisting of N-(2-nitro-4-aminophenyl)-allylamine (1.9 g, 0.01 mole), allyl bromide (2.4 g, 0.02 mole) and potassium carbonate (2.8 g, 0.02 mole) was boiled under reflux for 7 hours in 20 ml of ethanol. Working up was carried out in the same way as for compound 4. Yellow crystals, melting point 131°–140° C.

6. 3-Nitro-4-(2-methylallyl)-amino-aminobenzene

A mixture consisting of 4-fluoro-3-nitroaminobenzene (7.8 g, 0.05 mmole) and (2-methylallyl)-amine hydrochloride (0.05 mmole) was boiled under reflux for 8 hours in 100 ml of ethanol. The reaction product was then filtered under suction. Yellow crystals.

7. 3-Nitro-4-allylaminobenzoic acid

Synthesis and working up as for compound 1, but with 4-chloro-3-nitrobenzoic acid instead of 4-fluoro-3-nitroaminobenzene. Yellow crystals, melting point 195°–200° C.

Application Examples

Dyeing of textile fibers:

A multifiber fabric (Multifiberfabric #1, Loeffer Textilien, Nettersheim) was used for the dyeing of textile fibers. The fabric in question consists of six textile strips consisting of polyacrylonitrile, acetyl cellulose (triacetate), polyamide, silk, viscose acetate and wool.

0.5 g of the dye (compound 1, 2 or 4 to 7), 8 g of sodium sulfate decahydrate and 2 g of sodium carbonate were dissolved in 100 ml of water at 60° C. The multi-fiber fabric was then added to the dye bath. The dye bath was then heated to a temperature of 98° C. over a period of 45 minutes. This temperature was maintained for 1 hour, the water evaporated being continuously replaced. The dyed fabric was then rinsed first with cold water and then with hot water. The fabric was then boiled for 20 minutes in 250 ml of water containing 0.25 g of sodium lauryl sulfate and subsequently rinsed. Finally, the fabric was dried. The dyeing results are set out in Table 1.

TABLE 1

| Fiber type | 1 | 2 | 4 | 5 | 6 | 7 |
| --- | --- | --- | --- | --- | --- | --- |
| Polyacrylonitrile | Violet-brown | Dark violet | Deep magenta | Deep magenta | Grey-red | Pastel yellow |
| Triacetate | — | — | — | — | — | — |
| Polyamide | Violet | Grey-violet | Grey-violet | Lilac | Grey-magenta | Pastel yellow |
| Silk | Light brown | Grey-magenta | Grey-magenta | Magenta | Grey brown | Orange-white |

TABLE 1-continued

| Fiber type | 1 | 2 | 4 | 5 | 6 | 7 |
|---|---|---|---|---|---|---|
| Viscose acetate | — | — | — | — | — | — |
| Wool | Grey-ruby | Grey-violet | Dull violet | Grey-magenta | Grey-ruby | Dark yellow |

Dyeing of human hair

Compounds 8, 9 and 10 are substantive dyes known from the literature which are used for comparison:

(8) 3-Nitro-4-(2-hydroxyethyl)-amino-aminobenzene (9) 2-Nitro-p-phenylene diamine

(10) 3-Nitro-4-(2-hydroxyethyl)-amino-N,N-bis-(2-hydroxyethyl)-aminobenzene

Hair dye creams with the following composition were prepared:

| | |
|---|---|
| $C_{12-18}$ fatty alcohol | 10 g |
| $C_{12-14}$ fatty alcohol + EO sulfate, Na salt (28%) | 25 g |
| Water | 60 g |
| Compound 1-3, 7-10 | 1 g |
| Ammonium sulfate | 1 g |
| Conc. ammonia solution | to pH 9.5 |
| Water | ad 100 g |

The constituents were mixed with one another in the order shown. After compound 1, 2, 3, 7, 8, 9 or 10 had been added, the emulsion was adjusted to pH 9.5 with conc. ammonia solution and then made up with water to 100 g. The dye cream was applied to approximately 5 cm long tresses of standardized, 90% grey, but not especially pretreated human hair and left thereon for 30 minutes at 27° C. On completion of the dyeing process, the hair was rinsed, washed with a typical shampoo and then dried. The results of the dyeing tests are set out in Table 2.

Table 2 also shows the total color difference values of each dye finish. The total color difference is measured on level-dyeing tresses and provides information on the level-dyeing behavior of the dye.

Level-dyeing tresses are prepared by treating the upper half of a tress (i.e. the ends) for 30 minutes with an aqueous solution of a cold wave preparation based on ammonium thioglycolate. After fixing (10 minutes, potassium bromate solution, the tress half is washed and dried. It is then bleached with an aqueous solution of hydrogen peroxide and ammonium peroxydisulfate. The treatment with the cold wave preparation, fixing and bleaching are then repeated. The lower half of the hair tress (roots) is only bleached once. Two tress halves damaged to different extents are obtained in this way.

Level dyeing is expressed as DE values (total color difference between the two ends of the level-dyeing tress). The DE values are determined as follows:

Each level-dyeing tress is measured at eight places (4 in the vicinity of the roots and 4 in the vicinity of the ends) using a Datacolor color measuring system. To this end, the sample to be measured is fixed in the clamp of a spectral photometer and the reflectance values are measured over the visible light range from 390 to 700 nm at intervals of 10 nm and processed by computer (HP 2113 E Minicomputer). The computer program determines the standard color values under the CIE system (Commission Internationale de l'Eclairage) in accordance with DIN 5033 and converts them into color difference values according to DIN 6174.

TABLE 2

| Compound | Color of the dyed hair | Total color difference (DE value) |
|---|---|---|
| 1 | Violet-brown | 3.7 |
| 2 | Blue-violet | 7.4 |
| 3 | Purple | 4.1 |
| 7 | Dark olive-yellow | 6.1 |
| 8 | Purple-red | 12.56 |
| 9 | Orange-red | 19.9 |
| 10 | Red-violet | 15.75 |

We claim:

1. Aromatic allylaminonitro compounds corresponding to formula (I):

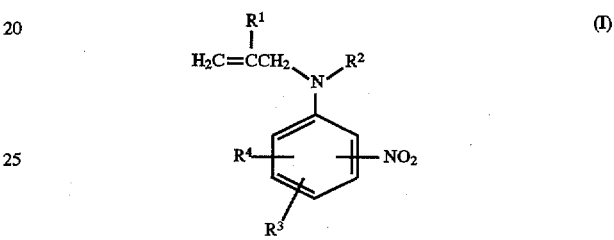

in which $R^1$ is hydrogen, $R^2$ is hydrogen, $R^3$ is carboxyl, hydroxy, nitro, halogen or a group $NR^6R^7$, where $R^6$ and $R^7$ are identical and represent hydrogen, an alkyl group containing 1 to 4 carbon atoms, a hydroxyalkyl or dihydroxyalkyl group containing 2 to 4 carbon atoms or an allyl group $CH_2C(R^8)=CH_2$, where $R^8$ is hydrogen or an alkyl group containing 1 to 4 carbon atoms, and $R^4$ is hydrogen or nitro, with the proviso that $R^3$ and $R^4$ are not both nitro, and when the $NO_2$ group is in the para position to the allylamino group $N(R^2)CH_2C(R^1)=CH_2$, $R^3$ is hydroxy and $R^4$ is hydrogen, and when the $NO_2$ group is in the ortho position to the allylamino group $N(R^2)CH_2C(R^1)=CH_2$, $R^3$ represents $NR^6R^7$ and is in the para position to the allylamino group $N(R^2)CH_2C(R^1)=CH_2$, and $R^4$ is hydrogen.

2. Aromatic allylaminonitro compounds as in claim 1 comprising 3-nitro-4-allyamino-aminobenzene.

3. The process of dyeing synthetic fibers or fibers of natural origin comprising contacting said fibers with a composition containig 0.01 to 5% by weight of aromatic allylaminonitro compounds corresponding to formula (I):

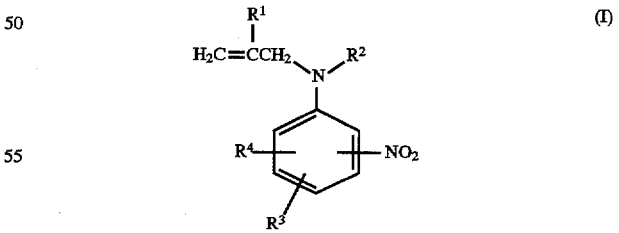

in which $R^1$ is hydrogen or an alkyl group containing 1 to 4 carbon atoms, $R^2$ is hydrogen, an alkyl group containing 1 to 4 carbon atoms or an allyl group $CH_2C(R^5)=CH_2$, where $R^5$ is hydrogen or an alkyl group containing 1 to 4 carbon atoms, $R^3$ is carboxyl, hydroxy, nitro, halogen or a group $NR^6R^7$, where $R^6$ and $R^7$ independently of one another represent hydrogen, an alkyl group containing 1 to 4 carbon atoms, a hydroxyalkyl or dihydroxyalkyl group containing 2 to 4 carbon atoms or an allyl group $CH_2C(R^8)=CH_2$, where $R^8$ is hydrogen or an alkyl group containing 1 to 4 carbon atoms, and $R^4$ is hydrogen or nitro, with the proviso that $R^3$ and $R^4$ are not both nitro, and when the $NO_2$ group is in the para position to the allylamino group $N(R^2)CH_2C(R^1)=CH_2$, $R^3$ is hydroxy and $R^4$ is hydrogen, and when the $NO_2$ group is in the ortho position to the allylamino group $N(R^2)CH_2C(R^1)=CH_2$, $R^3$ represents $NR^6R^7$ and is in the para position to the allylamino group $N(R^2)CH_2C(R^1)=CH_2$, and $R^4$ is hydrogen, and at least one component selected from the group consisting of wetting agents, emulsifiers, thickeners, perfume oils, water-soluble cationic polymers, water-soluble ampholytic polymers, water-soluble anionic polymers, protein derivatives, pantothenic acid, and cholesterol.

4. A process as in claim 3 wherein in said aromatic allylaminonitro compounds $R^1$ and $R^2$ are hydrogen and $R^6$ and $R^7$ are identical groups.

5. A process as in claim 3 wherein said aromatic allylaminonitro compounds comprise 3-nitro-4 allylamino-aminobenzene.

6. A process as in claim 3 wherein said fibers are keratin fibers.

7. A process as in claim 6 wherein said keratin fibers are human hair.

8. A hair dye composition containing 0.01 to 5% by weight of aromatic allylaminonitro compounds corresponding to formula (I):

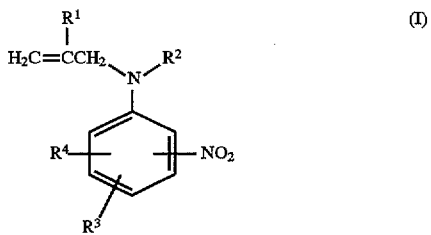

(I)

in which $R^1$ is hydrogen or an alkyl group containing 1 to 4 carbon atoms, $R^2$ is hydrogen, an alkyl group containing 1 to 4 carbon atoms or an allyl group $CH_2C(R^5)=CH_2$, where $R^6$ is hydrogen or an alkyl group containing 1 to 4 carbon atoms, $R^3$ is carboxyl, hydroxy, nitro. halogen or a group $NR^6R^7$, where $R^6$ and $R^7$ independently of one another represent hydrogen, an alkyl group containing 1 to 4 carbon atoms, a hydroxyalkyl or dihydroxyalkyl group containing 2 to 4 carbon atoms or an allyl group $CH_2C(R^8)=CH_2$, where $R^8$ is hydrogen or an alkyl group containing 1 to 4 carbon atoms, and $R^4$ is hydrogen or nitro, with the proviso that $R^3$ and $R^4$ are not both nitro, and when the $NO_2$ group is the para position to the allylamino group $N(R^2)CH_2C(R^1)=CH_2$, $R^3$ is hydroxy and $R^4$ is hydrogen, and when the $NO_2$ group is in the ortho position to the allylamino group $N(R^2)CH_2C(R^1)=CH_2$, $R^3$ represents $NR^6R^7$ and is in the para position to the allylamino group $N(R^2)CH_2C(R^1)=CH_2$, and $R^4$ is hydrogen, based on the weight of said hair dye composition, and at least one component selected from the group consisting of wetting agents, emulsifiers, thickeners, perfume oils, water-soluble cationic polymers, water-soluble ampholytic polymers, water-soluble anionic polymers, protein derivatives, panthenic acid, and cholesterol.

9. a composition as in claim 8 further containing a cosmetic carrier.

10. A composition as in claim 8 wherein in said aromatic allylaminonitro compounds $R^1$ and $R^2$ are hydrogen and $R^6$ and $R^7$ are identical groups.

11. A composition as in claim 8 wherein said aromatic allyaminonitro compounds corrosive 3-nitro-4-allylamino aminebenzene.

* * * * *